United States Patent [19]
Davis

[11] Patent Number: 4,661,433
[45] Date of Patent: Apr. 28, 1987

[54] STORAGE STABLE ARYL NITRONE COMPOSITIONS

[75] Inventor: Gary C. Davis, Albany, N.Y.

[73] Assignee: General Electric Company, Schenectady, N.Y.

[21] Appl. No.: 687,681

[22] Filed: Dec. 31, 1984

[51] Int. Cl.$^4$ .............. G03C 1/727; G03C 5/00; C07C 135/02

[52] U.S. Cl. .................... 430/270; 430/339; 430/394; 430/292; 564/297; 564/298; 564/299; 252/194

[58] Field of Search ............ 564/297, 298, 299; 252/194; 430/394, 339, 270, 292

[56] References Cited

U.S. PATENT DOCUMENTS 2,933,455  4/1960  Doying ........................ 252/194
4,508,631  4/1985  Packo et al. ................ 252/78.3 X

FOREIGN PATENT DOCUMENTS 0110165  6/1984  European Pat. Off. ............ 430/339

OTHER PUBLICATIONS

Jan Hamer and Anthony Macaluso, "Nitrones", *Chemical Reviews* vol. 64, No.4, Aug. 1964, pp. 473-495.
Staudinger et al., *Helv. Chim. Acta*, 2, 554-582 (1919).
Staudinger et al., *Chem. Abstracts*, 14, 1971-1972 (1920).

*Primary Examiner*—John E. Kittle
*Assistant Examiner*—Cynthia Hamilton
*Attorney, Agent, or Firm*—William H. Pittman; James C. Davis, Jr.; James Magee, Jr.

[57] ABSTRACT

Aryl nitrones, of the type used in contrast enhancement photolithography techniques, are stabilized by adding thereto a drying agent such as molecular sieve, silica gel or an alkylalkoxysilane. The resulting compositions are substantially storage stable.

20 Claims, 3 Drawing Figures

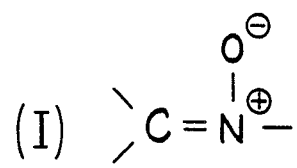
(I)
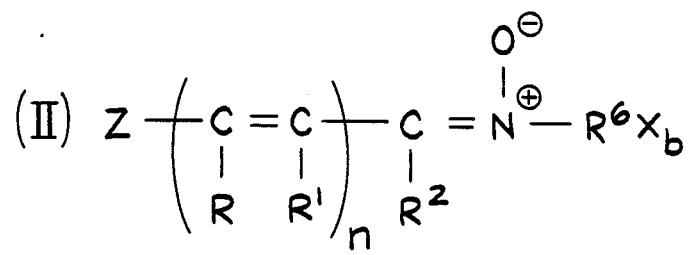
(II)
FIG. III
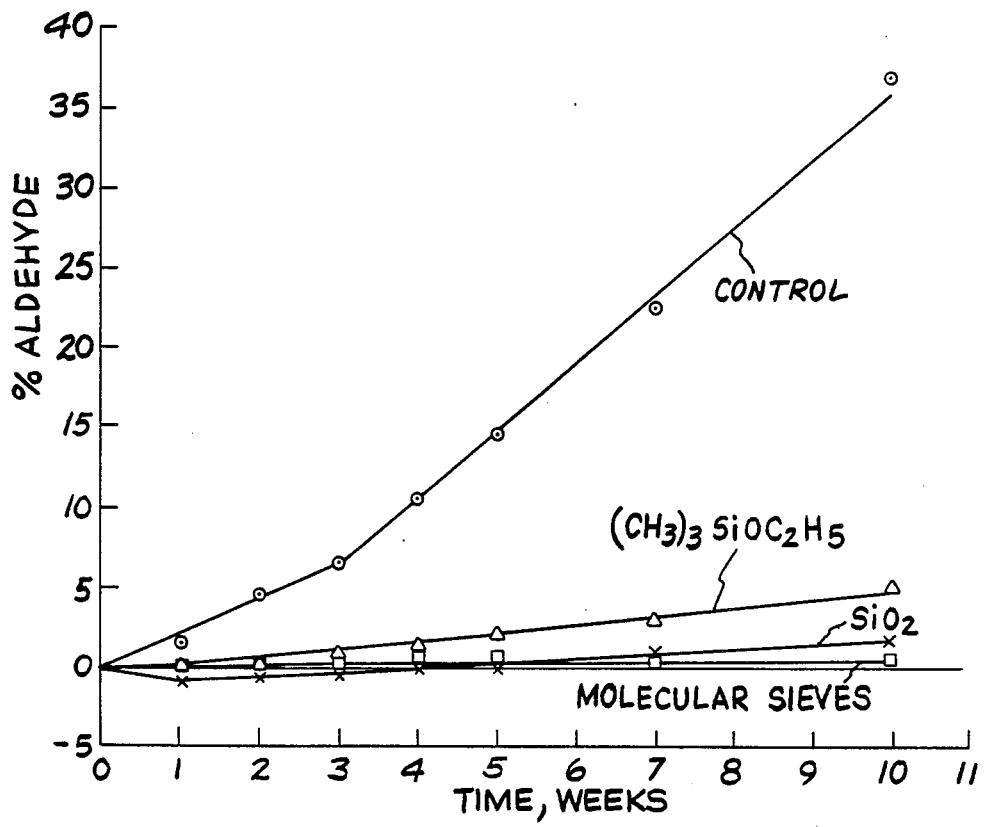

STORAGE STABLE ARYL NITRONE COMPOSITIONS

This invention relates to the stabilization of nitrone compositions. More particularly, it relates to storage stable aryl nitrone compositions and a method for preserving the storage stability of aryl nitrones.

Nitrones are a class of compounds containing the moiety represented by formula I in the drawings, wherein each of the free valence bonds is attached to a suitable organic radical. They are typically prepared by the reaction of an aldehyde with a hydroxylamine, most often in the presence of a catalyst such as a carboxylic acid. During the reaction, water is evolved. The reaction is one of equilibrium and is driven to the right by removal of water as it is formed. Aryl nitrones are useful as photobleachable compounds in photolithography techniques using contrast enhancement, as described in European patent application No. 110,165 and in co-pending, commonly assigned application Ser. No. 536,923, filed Sept. 28, 1983, the disclosures of which are incorporated by reference herein.

Aryl nitrones are extremely reactive compounds which tend to decompose upon storage. Like any other chemicals useful in industrial processes, they must be stored, sometimes for prolonged periods. It is therefore of great interest to increase their storage stability by inhibiting whatever decomposition reactions may occur.

A principal object of the present invention, therefore, is to provide storage stable aryl nitrone compositions.

A further object is to provide a method for stabilizing aryl nitrones.

Other objects will in part be obvious and will in part appear hereinafter.

The present invention is based on the discovery that a major contributing factor in the decomposition of aryl nitrones is the reverse of the reaction by which they are formed. Traces of water in contact with the nitrone hydrolyze it to the hydroxylamine and aldehyde. The hydroxylamine is then (at least partially) spontaneously oxidized by contact with air to the corresponding nitroso compound, which reacts with further hydroxylamine to form an azoxy compound and water. The water thus formed in turn reacts with further nitrone in a circular process which seriously decreases the activity of the nitrone composition.

BRIEF DESCRIPTION OF THE DRAWINGS

FIG. I is formula I representing the nitrone moiety.
FIG. II is formula II illustrating a class of aryl nitrones stabilized according to the present invention.

Accordingly, one aspect of the present invention is compositions with improved storage stability comrising at least one aryl nitrone and a drying agent which is substantially inert to said aryl nitrone. Another aspect is a method of stabilizing such nitrones which comprises contacting them with such drying agent.

The aryl nitrones which may be stabilized according to the present invention include those represented by formula II, wherein:

Z is $(R^3)_a$—Q—$R^4$— or $R^5$;
Q is a monovalent, divalent or trivalent substituent or linking group;
each of R, $R^1$, $R^2$ and $R^3$ is independently hydrogen, an alkyl or substituted alkyl radical containing 1–8 carbon atoms or an aromatic radical containing 6–13 carbon atoms;
$R^4$ is an aromatic radical containing 6–13 carbon atoms;
$R^5$ is an aromatic heterocyclic radical containing 6–20 carbon atoms in which the hetero atoms are at least one of oxygen, nitrogen and sulfur;
$R^6$ is an aromatic hydrocarbon radical containing 6–20 carbon atoms;
X is halo, cyano, aliphatic acyl, alkyl or substituted alkyl of 1–8 carbon atoms, aryl of 6–13 carbon atoms or carbalkoxy;
a is from 0 to 2;
b is from 0 to 3; and
n is from 0 to 4.

As is apparent from formula II, the nitrones may be α-aryl-N-arylnitrones or conjugated analogs thereof in which the conjugation is between the aryl group and and α-carbon atom. The α-aryl group is frequently substituted, most often by a dialkylamino group in which the alkyl groups contain 1–4 carbon atoms. The $R^2$ value is usually hydrogen and $R^6$ is usually phenyl.

The identity of the Q value is, for the most part, not critical and suitable values will be apparent to those skilled in the art. Obviously, Q will be monovalent, divalent or trivalent according as the value of a is 0, 1 or 2. Illustrative Q values are:

Monovalent: F, Cl, Br, I alkyl, aryl.
Divalent: O, S, carbonyl, alkylene, arylene.
Trivalent: N.
Preferably, Q is F, Cl, Br, I, O, S or N.

The following nitrones are illustrative of those which may be used in this invention;
α-(4-Diethylaminophenyl)-N-phenylnitrone
α-(4-Diethylaminophenyl)-N-(4-chlorophenyl)-nitrone
α-(4-Diethylaminophenyl)-N-(3,4-dichlorophenyl)-nitrone
α-(4-Diethylaminophenyl)-N-(4-carbethoxyphenyl)-nitrone
α-(4-Diethylaminophenyl)-N-(4-acetylphenyl)-nitrone
α-(4-Dimethylaminophenyl)-N-(4-cyanophenyl)-nitrone
α-(4-Methoxyphenyl)-N-(4-cyanophenyl)nitrone
α-(9-Julolidinyl)-N-phenylnitrone
α-(9-Julolidinyl)-N-(4-chlorophenyl)nitrone
α-[2-(1,1-Diphenylethenyl)]-N-phenylnitrone
α-[2-(1-Phenylpropenyl)]-N-phenylnitrone.

An especially preferred aryl nitrone is α-(4-diethylaminophenyl)-N-phenylnitrone.

The proportion of drying agent in the compositions of this invention is not critical and may be adjusted as necessary to inhibit hydrolytic decomposition of the nitrone. Most often, the weight ratio of drying agent to nitrone will be from about 0.25:1 to about 5.0:1.

In addition to the aryl nitrone and the drying agent hereinafter described, the compositions of this invention generally contain a solvent, most often a solvent suitable for use in providing a spin-coatable mixture. Illustrative solvents are aromatic hydrocarbons such as toluene, xylene and ethylbenzene, halogenated aromatic hydrocarbons such as chlorobenzene, mixtures thereof with aliphatic or alicyclic hydrocarbons such as n-heptane and cyclohexane, halogenated aliphatic compounds such as trichloroethylene and methylchloroform, and alcohols such as 1-propanol, 2-propanol and 1-butanol. The aromatic hydrocarbons are preferred.

It is also commonplace to include in the composition a substantially inert organic polymer binder. Suitable polymers for this purpose include polystyrene, poly($\alpha$-methylstyrene), copolymers of styrene with such monomers as vinylpyridine and allyl alcohol, poly(methyl methacrylate), poly(hydroxyethyl methacrylate) and poly(vinylpyrolidone).

According to the present invention, a drying agent is incorporated in the above-described composition. The drying agent may be liquid or solid. It should be inert to the aryl nitrone and, in general, should form nondeleterious materials upon interaction with water. Thus, a solid, insoluble drying agent may interact with water to form other solids; but for the most part, a liquid should not interact to form solids which precipitate from the composition. Preferably, liquid drying agents should react to form materials easily removed by volatilization upon further processing. When a polymer is also present in the composition, the drying agent should not deleteriously react with said polymer, although the use of a drying agent which reacts in some way with said polymer is not precluded so long as the reaction is reversible or harmless.

Illustrative drying agents are molecular sieves, silica gel and alkylalkoxysilanes of the formula $(R^7)_m Si(OR^8)_p$, wherein $R^7$ and $R^8$ are lower alkyl radicals (i.e., alkyl radicals containing up to 7 carbon atoms), preferably $C_{1-4}$ alkyl radicals and more preferably methyl or ethyl, and $m+p=4$.

The most useful alkylalkoxysilanes are those in which m is 3 and n is 1, and especially trimethylethoxysilane. It reacts with water to yield trimethylsilanol and ethanol; the trimethylsilanol may subsequently condense to the relatively volatile hexamethyldisiloxane with the evolution of one-half mole of water. Thus, the total water uptake is one-half to one mole per mole of trimethylethoxysilane. (Trimethylethoxysilane reacts with some polymers containing hydroxy groups, but the product is a polymeric trimethylalkoxysilane or the like which itself reacts with water to regenerate the original polymer.)

Also useful under some circumstances are dialkyldialkoxysilanes. However, they are less preferred since their reaction product with water is a dialkyldihydroxysilane, which may polymerize to form an insoluble material which must be removed by filtration or the like, or which remains on the substrate after spin-coating and solvent removal.

Certain suitable drying agents such as molecular sieves and silica gel may exist in such finely divided condition that their removal from the composition prior to spin-coating is difficult. In such cases, it may be desirable to enclose the drying agent in a liquid-permeable container such as fine-mesh cloth. It is also possible to use such drying agents as silica gel in the form of relatively large beads which are easily separable from the solution.

It will be apparent to those skilled in the art that the compositions of this invention may be conveniently stored under normal conditions. When they are to be used, any solid drying agent is removed by conventional methods such as those described hereinabove.

The invention is illustrated by a procedure in which ethylbenzene solutions of 200 mg. of $\alpha$-(4-diethylaminophenyl)-N-phenylnitrone were stored under atmospheric conditions in contact with 200 mg. of trimethylethoxysilane, 500 mg. of 4-Angstrom molecular sieves and 500 mg. of desiccant silica beads, respectively. The solutions were stored for 10 weeks, with periodic analysis by high pressure liquid-liquid chromatography to determine the aldehyde content thereof.

The results are shown in FIG. III, in comparison with a control containing no drying agent. (The initial aldehyde value was arbitrarily set at 0, which accounts for the negative aldehyde readings; any aldehyde originally present was removed, either by adsorption or the drying agent or by reaction with the hydroxylamine as a result of the nitrone-forming reaction being driven to the right by removal of water.) It is apparent that the compositions of this invention are much more storage stable than the control.

It was also found that solutions in 35 grams of ethylbenzene of 2 grams of $\alpha$-(4-diethylaminophenyl)-N-phenylnitrone, 2 grams of a styrene-allyl alcohol copolymer and 2 grams of trimethylethoxysilane were suitable for use in contrast enhancement, as described in the aforementioned application Ser. No. 536,923, even after long periods of storage.

What is claimed is:

1. A composition comprising at least one aryl nitrone and a drying agent which is substantially inert to said aryl nitrone.

2. A composition according to claim 1 which also comprises a solvent suitable for use in providing a spin-coatable mixture.

3. A composition according to claim 2 wherein the drying agent is a molecular sieve, silica gel or an alkylalkoxysilane of the formula $(R^7)_m Si(OR^8)_p$, wherein $R^7$ and $R^8$ are lower alkyl radicals and $m+p=4$.

4. A composition according to claim 3 which also comprises a substantially inert polymeric binder.

5. A composition according to claim 4 wherein the aryl nitrone has formula II in the drawings, wherein:

Z is $(R^3)_a$—Q—$R^4$— or $R^5$;

Q is a monovalent, divalent or trivalent substituent or linking group;

each of R, $R^1$, $R^2$ and $R^3$ is independently hydrogen, an alkyl or substituted alkyl radical containing 1-8 carbon atoms or an aromatic radical containing 6-13 carbon atoms;

$R^4$ is an aromatic radical containing 6-13 carbon atoms;

$R^5$ is an aromatic heterocyclic radical containing 6-20 carbon atoms in which the hetero atoms are at least one of oxygen, nitrogen and sulfur;

$R^6$ is an aromatic hydrocarbon radical containing 6-20 carbon atoms;

X is halo, cyano, aliphatic acyl, alkyl or substituted alkyl or 1-8 carbon atoms, aryl of 6-13 carbon atoms or carbalkoxy;

a is from 0 to 2;

b is from 0 to 3; and n is from 0 to 4.

6. A composition according to claim 5 wherein $R^2$ is hydrogen, $R^6$ is phenyl and Q is F, Cl, Br, I, O, S or N.

7. A composition according to claim 6 wherein the nitrone is $\alpha$-(4-diethylaminophenyl)-N-phenylnitrone.

8. A composition according to claim 7 wherein the drying agent is a molecular sieve.

9. A composition according to claim 7 wherein the drying agent is silica gel.

10. A composition according to claim 7 wherein the drying agent is an alkylalkoxysilane wherein m is 3, p is 1 and each of $R^7$ and $R^8$ is methyl or ethyl.

11. A method of stabilizing an aryl nitrone-containing composition which comprises maintaining said composition in contact with a drying agent which is substantially inert to said nitrone.

12. A method according to claim 11 wherein said composition also comprises a solvent suitable for use in providing a spin-coatable mixture.

13. A method according to claim 12 wherein the drying agent is a molecular sieve, silica gel or an alkylalkoxysilane of the formula $(R^7O)_m Si(OR^8)_p$, wherein $R^7$ and $R^8$ are lower alkyl radicals and $m+p=4$.

14. A method according to claim 13 wherein said composition also comprises a substantially inert polymeric binder.

15. A method according to claim 14 wherein the aryl nitrone has formula II in the drawings, wherein:

Z is $(R^3)_a-Q-R^4-$ or $R^5$;

Q is a monovalent, divalent or trivalent substituent or linking group;

each of R, $R^1$, $R^2$ and $R^3$ is independently hydrogen, an alkyl or substituted alkyl radical containing 1-8 carbon atoms or an aromatic radical containing 6-13 carbon atoms;

$R^4$ is an aromatic radical containing 6-13 carbon atoms;

$R^5$ is an aromatic heterocyclic radical containing 6-20 carbon atoms in which the hetero atoms are at least one of oxygen, nitrogen and sulfur;

$R^6$ is an aromatic hydrocarbon radical containing 6-20 carbon atoms;

X is halo, cyano, aliphatic acyl, alkyl or substituted alkyl of 1-8 carbon atoms, aryl of 6-13 carbon atoms or carbalkoxy;

a is from 0 to 2;

b is from 0 to 3; and n is from 0 to 4.

16. A method according to claim 15 wherein the nitrone is α-(4-diethylaminophenyl)-N-phenylnitrone.

17. A method according to claim 16 wherein the drying agent is a molecular sieve.

18. A method according to claim 16 wherein the drying agent is silica gel.

19. A method according to claim 16 wherein the drying agent is an alkylalkoxysilane wherein m is 3, p is 1 and each of $R^7$ and $R^8$ is methyl or ethyl.

20. A method according to claim 15 wherein said drying agent is enclosed in a liquid-permeable container.

* * * * *